(12) United States Patent
Summers et al.

(10) Patent No.: US 10,209,227 B2
(45) Date of Patent: Feb. 19, 2019

(54) METHOD AND APPARATUS FOR INSPECTING A PART HAVING A NON-LINEAR CROSS-SECTION

(71) Applicant: The Boeing Company, Chicago, IL (US)

(72) Inventors: Kate Summers, Seattle, WA (US); Fred D. Young, Bellevue, WA (US); Joseph Taylor, Pacific, WA (US)

(73) Assignee: The Boeing Company, Chicago, IL (US)

( * ) Notice: Subject to any disclaimer, the term of this patent is extended or adjusted under 35 U.S.C. 154(b) by 169 days.

(21) Appl. No.: 15/015,223

(22) Filed: Feb. 4, 2016

(65) Prior Publication Data
US 2017/0227504 A1 Aug. 10, 2017

(51) Int. Cl.
*G01N 29/27* (2006.01)
(52) U.S. Cl.
CPC ................... *G01N 29/27* (2013.01)
(58) Field of Classification Search
CPC ........................................... G01N 29/27
USPC .......................................................... 73/634
See application file for complete search history.

(56) References Cited

U.S. PATENT DOCUMENTS

| 5,007,291 | A | * | 4/1991 | Walters | G01N 29/043 226/176 |
|---|---|---|---|---|---|
| 6,722,202 | B1 | * | 4/2004 | Kennedy | G01N 29/225 73/634 |
| 2006/0053892 | A1 | * | 3/2006 | Georgeson | G01N 29/24 73/634 |
| 2006/0162456 | A1 | * | 7/2006 | Kennedy | G01N 29/225 73/620 |
| 2008/0236286 | A1 | * | 10/2008 | Lam | G01N 29/043 73/618 |
| 2008/0314154 | A1 | * | 12/2008 | Fetzer | G01N 29/2468 73/638 |
| 2009/0211361 | A1 | * | 8/2009 | Young | G01N 29/041 73/620 |
| 2011/0083512 | A1 | * | 4/2011 | Imbert | G01N 29/0645 73/622 |
| 2011/0257903 | A1 | * | 10/2011 | Imbert | G01M 13/045 702/35 |
| 2013/0160309 | A1 | * | 6/2013 | Logan | G01B 11/00 33/228 |

* cited by examiner

*Primary Examiner* — Natalie Huls
*Assistant Examiner* — Monica S Young
(74) *Attorney, Agent, or Firm* — Perman & Green, LLP (57) ABSTRACT

In accordance with one or more aspects of the present disclosure, an apparatus for inspecting a part having a non-linear cross section includes a stationary sensor element including at least one phased array sensing unit, each of the at least one phased array sensing unit having a shape that is geometrically complimentary to the non-linear cross section of the part, and a support for the part having the non-linear cross section, the support comprising a drive assembly configured to move the part relative to the stationary sensor element, through an inspection beam emitted from the at least one phased array sensing unit.

20 Claims, 11 Drawing Sheets

METHOD AND APPARATUS FOR INSPECTING A PART HAVING A NON-LINEAR CROSS-SECTION

FIELD

The aspects of exemplary embodiment generally relate to inspecting parts, more particularly, to inspecting parts having a non-linear cross-section.

BACKGROUND

Components and parts employed in, for example, the aerospace, maritime or automotive industries, are typically inspected for quality and defects prior to being used in manufacturing. This is particularly true for composite, resin or polycarbonate components or structures. These components or structures are often part of window frames, door frames or other components which are designed to withstand shear forces or stresses. To prevent failure of these components, inspection systems are typically employed to inspect these components for porosity, potential delaminations, foreign artifacts or other defects affecting the structural integrity of the component. Often, these components have non-linear cross-sections which include both linear and curved portions, rendering inspection difficult. Further exacerbating the difficulty of inspecting these components, some of these components are in closed loop configurations (e.g. having a looped shape, for example, a window frame for an airplane). Additionally, inspection systems should detect defects and anomalies within these components non-destructively, without disturbing or damaging the component.

Prior art solutions (for example, the part scanner 200 shown in FIGS. 2A-2C) typically use a pair of flat phased arrays 201a, 201b arranged on opposing sides of a cross-section of the component 203. The flat phased arrays 201a, 201b are generally configured to operate in Through-Transmission Ultrasonic mode (TTU). One of the pair of flat phased arrays 201a, 201b transmits an ultrasonic signal and one of the pair of flat phased arrays 201a, 201b receives the ultrasonic signal as the ultrasonic signal passes through the component 203. However, using the pair of flat phased arrays 201a, 201b in TTU mode renders foreign material detection within the component 203 difficult. Further, the pair of flat phased arrays 201a, 201b in TTU mode has limited inspection coverage along the radii of a curved cross-section of the component 203, as well as the joggle (e.g. the inflection point or surface) of the component 203. In some configurations, there are multiple pairs of flat phased arrays (e.g. phased arrays 202a, 202b) operating in TTU mode in conjunction with the pair of flat phased arrays 201a, 201b to enhance the inspection coverage along the radii of a curved cross-section of the component 203. However, multiple pairs of flat phased arrays (201a, 201b and 202a, 202b) increases the complexity of the prior art solutions and increases the likelihood of downtime due to maintenance.

Figure 2A:
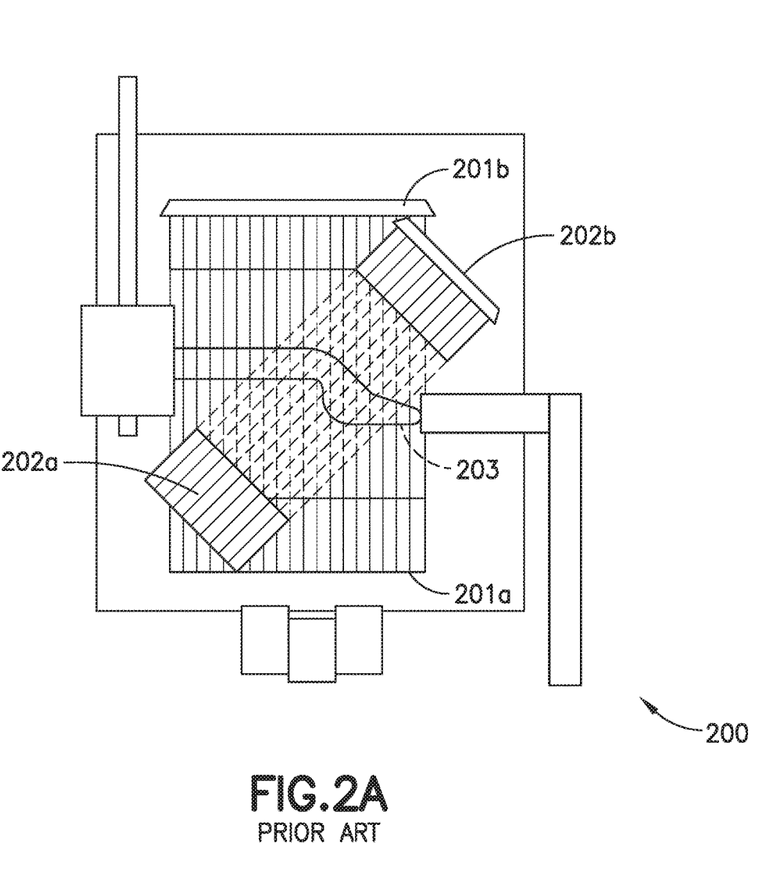
FIGS. 2A-2C are exemplary illustrations of a prior art inspection system.
Figure 2B:
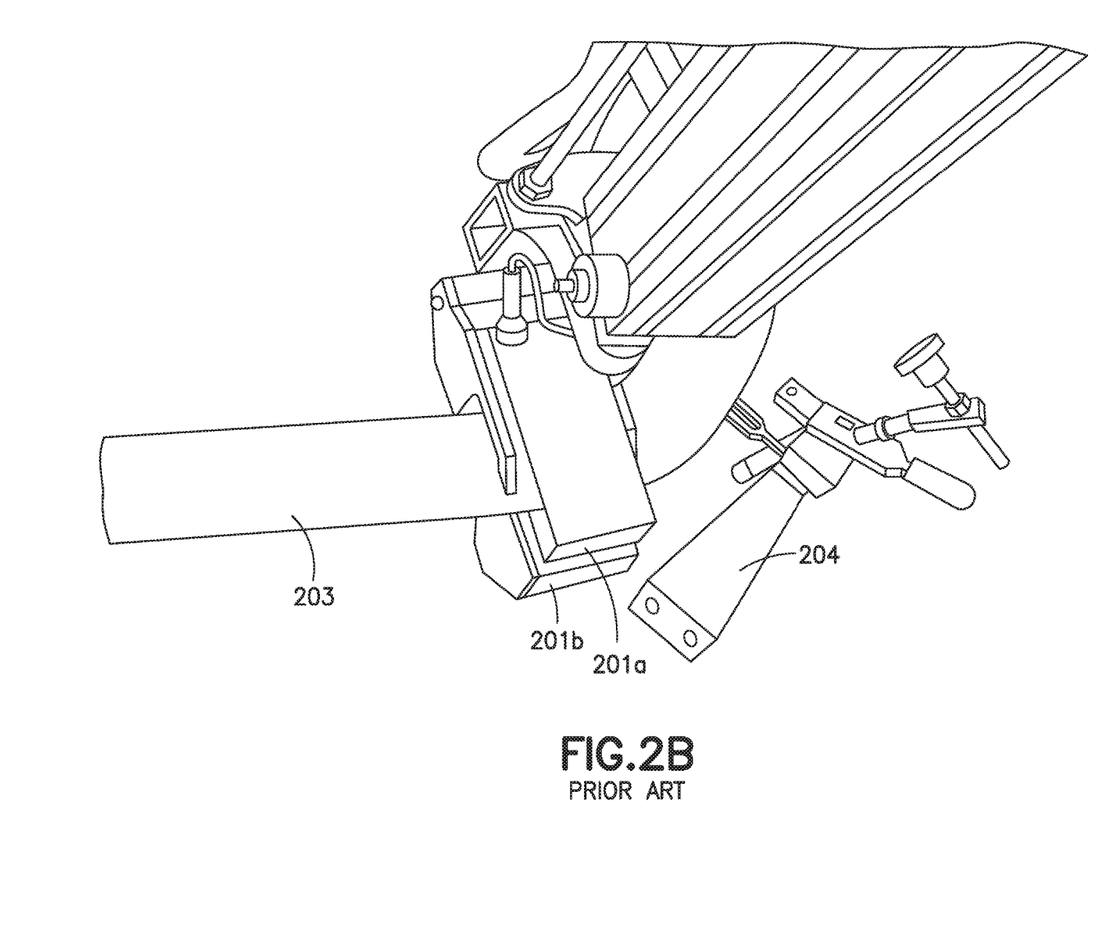
Figure 2C:
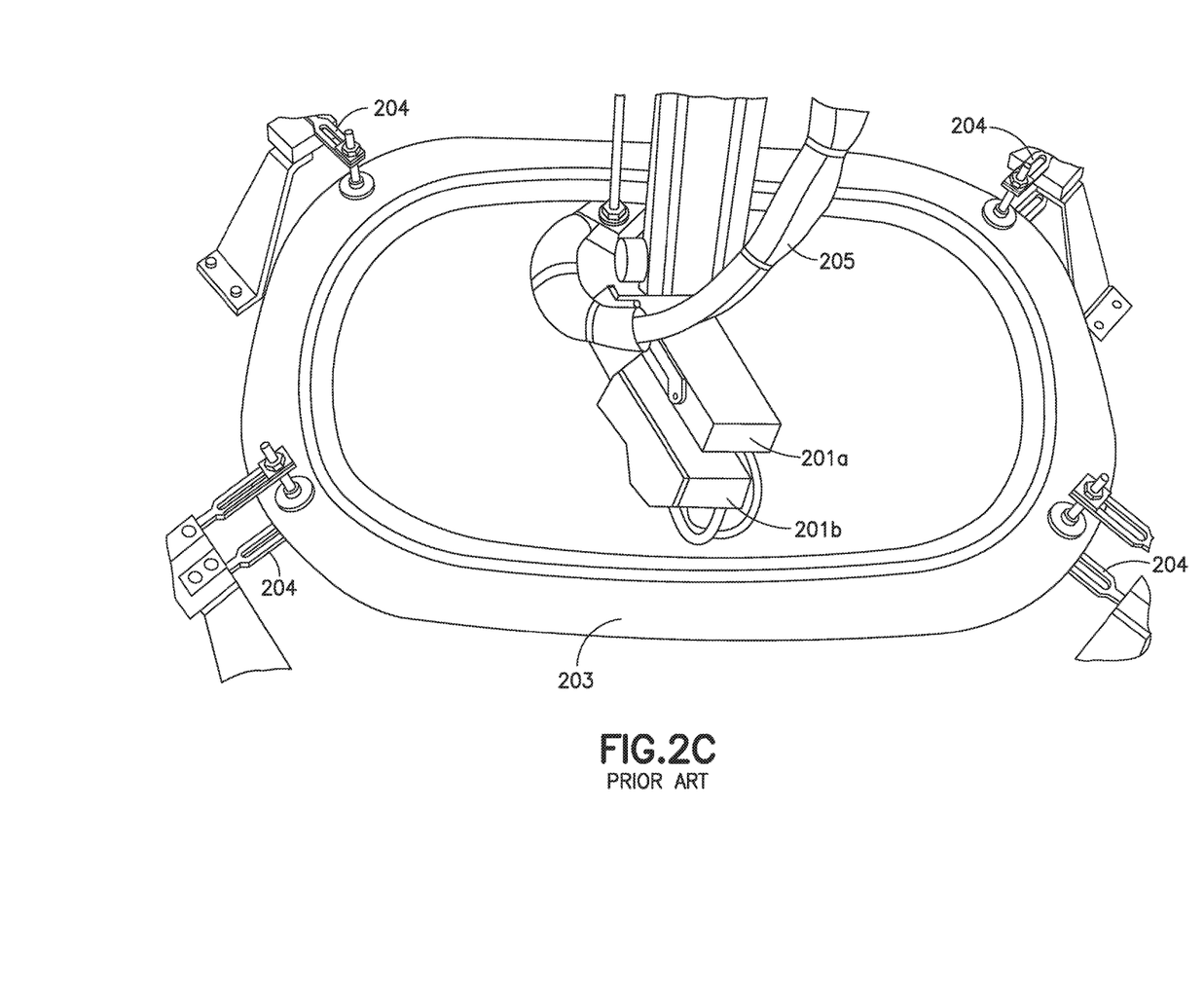

Further with respect to the prior art solutions shown in FIGS. 2A-2C, the entire component 203 is clamped to stationary clamps 204, which hold the component 203 while the pair of flat phased arrays 201a, 201b is moved along the length of the component 203. For components 203 with a closed looped structure, this arrangement is especially troublesome. Within this configuration, the clamps 204 are opened and closed manually to accommodate the pair of flat phased arrays 201a, 201b as they are moved past each clamp 204. The movement of the pair of flat phased arrays 201a, 201b around the looped structure of the component 204 further causes the cables connected to the pair of flat phased arrays 201a, 201b to become twisted after one or more rotations, resulting in frequent scanning stoppages or delays to untangle the cables (see FIG. 2C, where the cable 205 is twisted after rotating the pair of flat phased arrays 201a, 201b).

SUMMARY

Accordingly, a system and method, intended to address the above-identified concerns, would find utility.

In accordance with one or more aspects of the present disclosure, an apparatus for inspecting a part having a non-linear cross section includes a stationary sensor element including at least one phased array sensing unit, each of the at least one phased array sensing unit having a shape that is geometrically complimentary to the non-linear cross section of the part, and a support for the part having the non-linear cross section, the support comprising a drive assembly configured to move the part relative to the stationary sensor element, through an inspection beam emitted from the at least one phased array sensing unit.

In accordance with one or more aspects of the present disclosure, a system for inspecting a part having a non-linear cross section includes a stationary sensor element including at least one phased array sensing unit, each of the at least one phased array sensing unit having a shape that is geometrically complimentary to the non-linear cross section of the part, a support for the part having the non-linear cross section, the support comprising a drive assembly configured to move the part relative to the stationary sensor element, through an inspection beam emitted from the at least one phased array sensing unit, and a controller connected to the stationary sensor element and the drive assembly, the controller being configured to receive scan data from the stationary sensor element corresponding to the part.

In accordance with one or more aspects of the present disclosure, a method for inspecting a part having a non-linear cross section includes providing a stationary sensor element including at least one phased array sensing unit having a shape that is geometrically complimentary to the non-linear cross section of the part, positioning the part in relation to the stationary sensor element such that an inspection beam emitted from the at least one phased array sensing unit is focused on an inspection area of the part having the non-linear cross section, and moving the part relative to the stationary sensor element through the inspection beam emitted from the at least one phased array sensing unit.

BRIEF DESCRIPTION OF THE DRAWINGS

Having thus described examples of the disclosure in general terms, reference will now be made to the accompanying drawings, which are not necessarily drawn to scale, and wherein like reference characters designate the same or similar parts throughout the several views, and wherein:

In the block diagram(s) referred to above, solid lines, if any, connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. Couplings or connections other than those depicted in the block diagrams may also exist. Dashed lines, if any, connecting the various elements and/or components represent couplings or connections similar in function and purpose to those represented by solid lines; however, couplings or connections represented by the dashed lines may either be selectively provided or may relate to alternative or optional aspects of the disclosure. Likewise, elements and/or components, if any, represented with dashed lines, indicate alternative or optional aspects of the disclosure. Environmental elements, if any, are represented with dotted lines.

In the block diagram(s) referred to above, the blocks may also represent operations and/or portions thereof. Lines connecting the various blocks do not imply any particular order or dependency of the operations or portions thereof.

DETAILED DESCRIPTION

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting. It is further noted that all numbers, temperatures, etc. are "about" and provided for exemplary purposes only. All specific numbers, temperatures and any other specific information may be more or less or any suitable number or temperature.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Figure 3A:
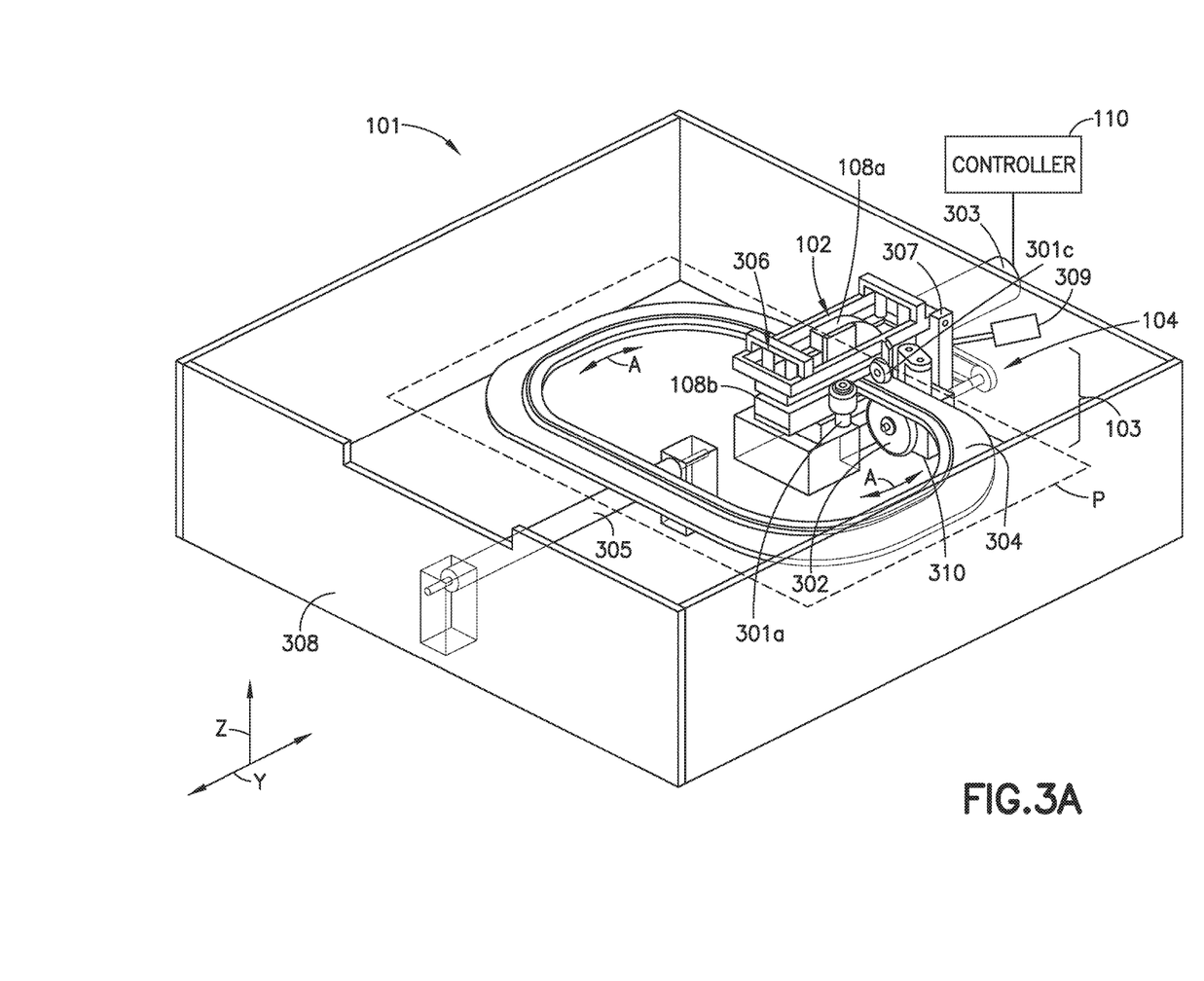
FIG. 3A is an exemplary perspective illustration of the inspection system according to aspects of the present disclosure.
Figure 3B:
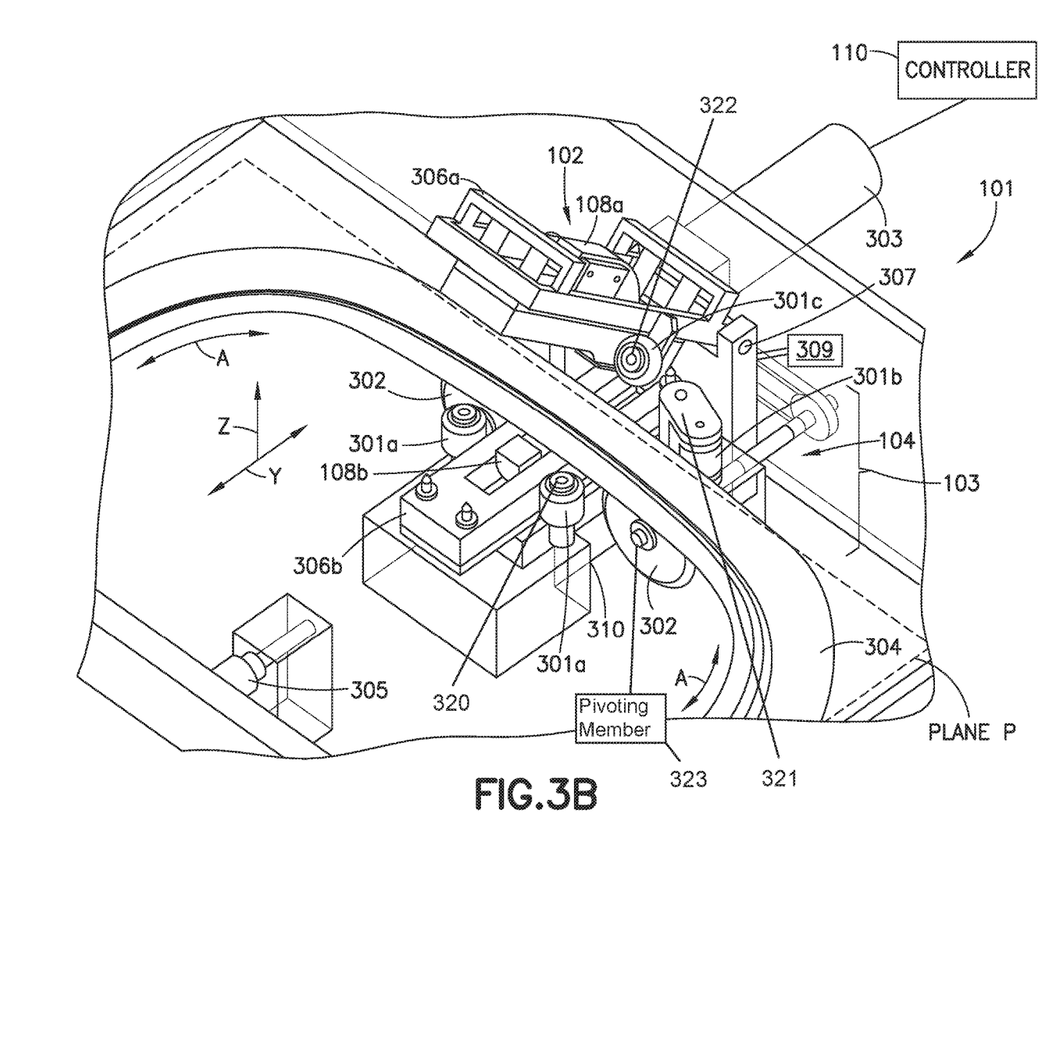
FIG. 3B is an exemplary perspective illustration of a portion of the inspection system according to aspects of the present disclosure.
Figure 4A:
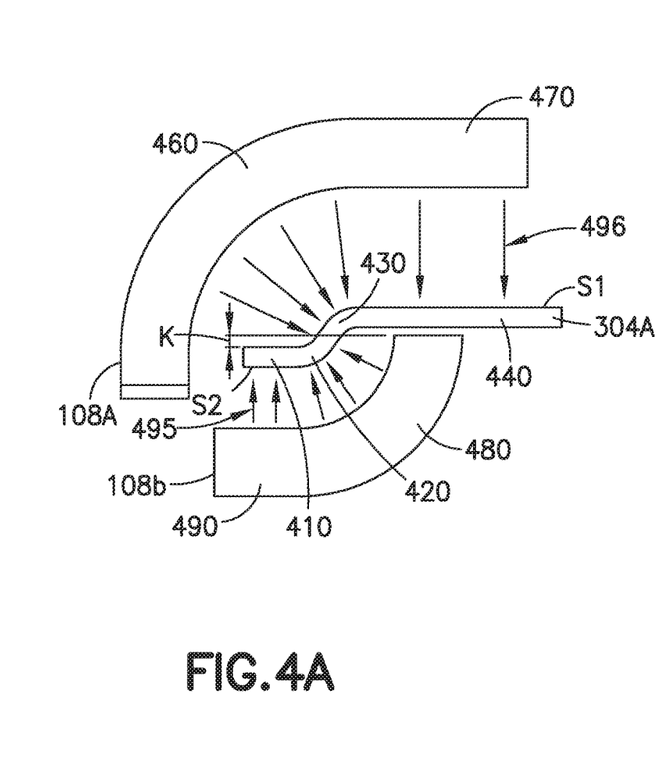
FIGS. 4A-4B are exemplary illustrations of a portion of the inspection system according to aspects of the present disclosure.
Figure 4B:
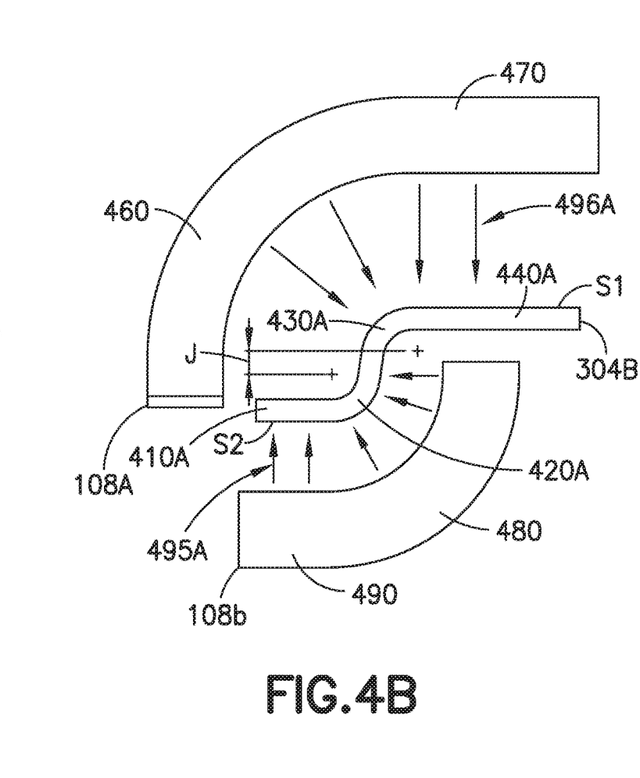

Referring now to FIGS. 1, 3A-3B and 4A-4B, an inspection system 100 for inspecting a part 304 having a non-linear cross-section is shown. In one aspect, the part 304 is shown in FIG. 3A and 3B as having a closed looped structure, but in other aspects, the part 304 can have any suitable shape, including curved or straight shapes. The part 304 further has a non-linear cross-section. In one aspect, the non-linear cross-section is a unitary one-piece structure that has both linear and curved portions contiguously joined together to form the non-linear cross-section. For example, the non-linear cross-section may have a Z-beam configuration having two straight portions joined by at least two curved portions while in other aspects, the non-linear cross-section may have any suitable configuration such as a J-beam configuration having at least one straight portion and at least one curved portion. In FIGS. 4A and 4B, two exemplary variants of the part 304 are shown as parts 304A, 304B for illustration purposes only, each of the parts 304A, 304B having a different cross-section and configuration. For example, part 304B includes at least one substantially 90 degree angle in the cross-section and a distance J between the centers of the radii of curved portions 420A and 430A. The part 304A includes at least one angle less than about 90 degrees in the cross-section and a distance K between the centers of the radii of curved portions 420 and 430 that is smaller than the distance J. As shown in FIGS. 4A and 4B, the cross-section of the parts 304A, 304B each have two curved portions (e.g. curved portions 420, 430 and 420A, 430A) and at least two flat portions (e.g. flat portions 410, 440 and 410A, 440A) substantially forming a Z-beam cross-section. In one aspect, such a Z-beam cross section is employed in, for example, vehicle window and door frames. In other aspects, the part 304 has any non-linear cross-section.

Figure 1:
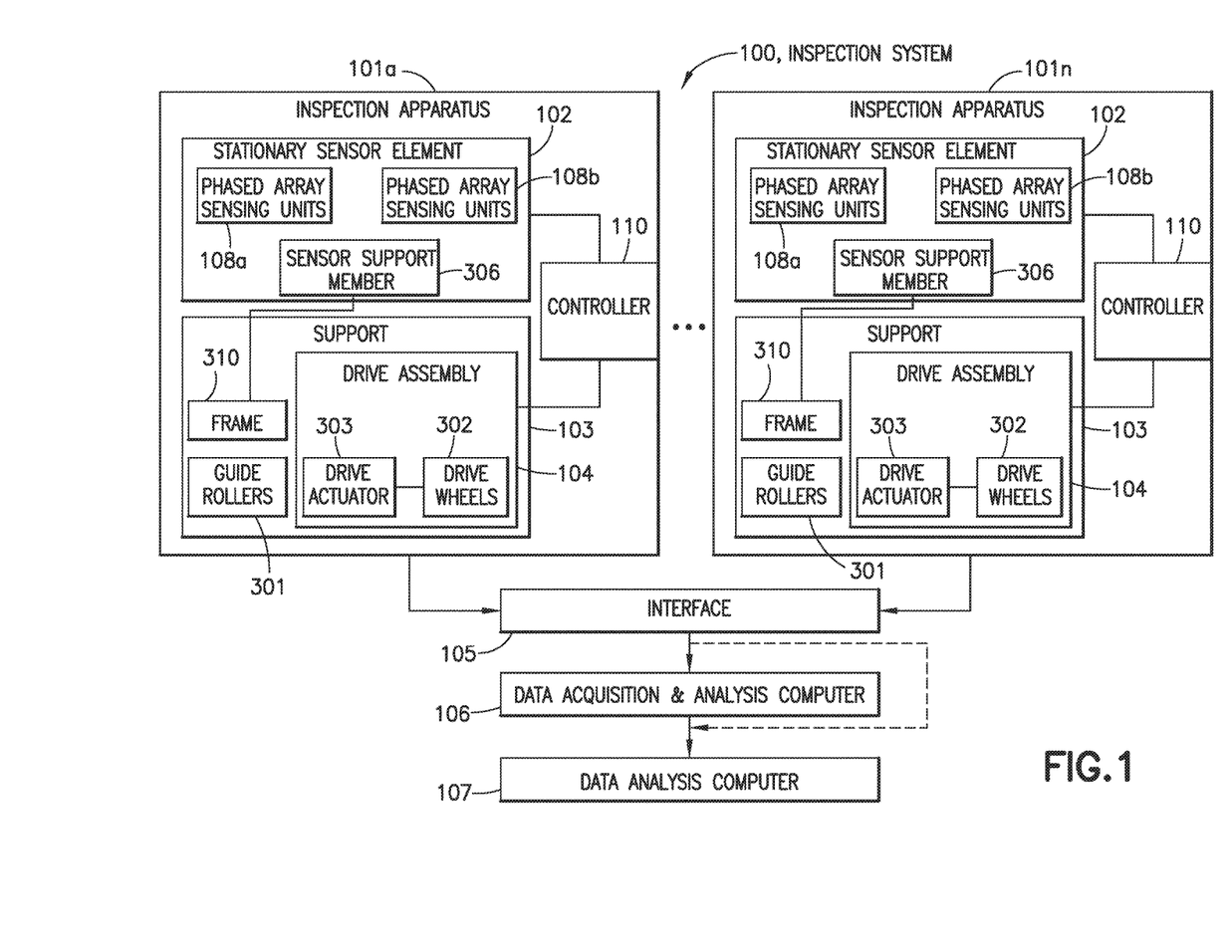
FIG. 1 is an exemplary block diagram of the inspection system according to aspects of the present disclosure.

The inspection system 100 includes one or more inspection apparatuses 101a-101n (generally referred to as inspection apparatus 101). Each inspection apparatus 101 includes a stationary sensor element 102 and a support 103. The stationary sensor element 102 includes one or more phased array sensing units 108a-108b (or other suitable sensing units having any suitable sensors) configured to emit an ultrasonic inspection beam for scanning the part 304 and a sensor support member 306. In one aspect, the inspection apparatus 101 further includes one or more controller(s) 110 connected to the stationary sensor element 102 and/or the support 103 and configured to control one or more operations of the stationary sensor element 102 and/or the drive assembly 104. The inspection apparatus 101 is further communicably connected to an interface 105. The interface 105 connects the inspection apparatus 101 to one or more data acquisition and data analysis computer 106 and/or data analysis computer 107, which will be described in greater detail below.

The stationary sensor element 102 interfaces with the part 304 and has one or more phased array sensing units 108a, 108b configured to scan the part 304 for inspection of the part 304. In one aspect, the stationary sensor element 102 maintains position relative to the direction normal to the cross section of the part 304 (e.g. the sensor element remains fixed relative to a frame 310, described below, of the inspection apparatus 101 while the part is moved through or relative to the stationary sensor element 120). In one aspect, the stationary sensor element 102 may be movable in accordance with the interface with the part 304. In one aspect, the examples shown in FIGS. 1, 3A-3B and 4A-4B show a stationary sensor element 102 with the two phased array sensing units 108a and 108b. In other aspects, the stationary sensor element 102 can have any number of phased array sensing units. In one aspect, the two phased array sensing units 108a, 108b are positioned or arranged on opposite sides of the part 304 (e.g. the sensing units 108a, 108b oppose each other), and are each configured to scan a respective side of the part 304. The placement of the two phased array sensing units 108a, 108b further enable both sides of the part 304 to be scanned at the same time. In one aspect, the two phased array sensing units 108a, 108b each have a shape that is geometrically complimentary to the non-linear cross-section of the part 304. The geometrically complimentary shape of the two phased array sensing units 108a, 108b provides for the part 304 to move relative to the stationary sensor element 102 (e.g. passing through or between the two phased array sensing units 108a, 108b) during the inspection process while emitting an ultrasonic inspection beam, from each of the two phased array sensing units 108a, 108b, that is arranged substantially perpendicular to the part 304 over substantially the entire inspection surface area of the part 304. In one aspect, the inspection surface area is the surface area of the cross-section of the part 304 passing through and being inspected by the ultrasonic inspection beam. In one aspect, the ultrasonic inspection beam is a Pulse/Echo ultrasonic signal however, in other aspects, the ultrasonic inspection beam is any suitable signal, including a TTU signal. In one aspect, the ultrasonic inspection beam is employed to non-destructively detect porosity, delaminations, foreign materials or other defects and anomalies within the part 304.

Referring now to FIGS. 4A and 4B, two exemplary schematic views of the two phased array sensing units 108a, 108b are shown for scanning the parts 304A, 304B for inspection, as previously described. As shown in FIGS. 4A and 4B, the two phased array sensing units 108a, 108b are in the form of J-shaped arrays, where each of the phased array sensing units 108a, 108b has a curved portion 460, 480 and a straight portion 470, 490 extending from an end of the curved portion 460, 480. In one aspect, the curved portion 460, 480 of each phased array sensing unit 108a, 108b has a radius that is substantially concentric with a radius of a curved portion 420, 430 and 420A, 430A of the parts 304A, 304B when the part 304A, 304B are held in the stationary sensor element 102 and the phased array sensing units 108a, 108b are closed around the parts 304A, 304B in an inspection position. The substantially straight portion 470, 490 of each phased array sensing unit 108a, 108b is substantially parallel to the straight portion 410, 440 and 410A, 440A of the parts 304A, 304B. In one aspect, the exemplary aspect shown in FIGS. 4A and 4B provides for each phased array sensing unit 108a, 108b to emit the ultrasonic inspection beam at an angle that is substantially perpendicular (e.g. a normal angle) to every point on the surface S1, S2 of the parts 304A, 304B facing a respective phased array sensing unit 108a, 108b (see ultrasonic inspection beams 495, 496 and 495A, 496A directed at surface S1, S2 of parts 304A, 304B). The transmission of the ultrasonic inspection beam at normal angle optimizes the pulse echo signal received from 304A and 304B. As shown in FIGS. 4A and 4B and as noted above, the parts 304A, 304B have a Z-beam configuration with two curved portions 420, 430 and 420A, 430A and two straight portions 410, 440 and 410A, 440A. The curved portions 460, 480 of the phased array sensing units 108a, 108b are concentric with a respective radii of a respective one of the curved portions 420, 430 and 420A, 430A of parts 304A, 304B. The straight portions 470, 490 of phased array sensing units 108a, 108b are parallel to a respective straight portion 410, 440 and 410A, 440A of parts 304A, 304B. In other aspects, the parts 304A, 304B have any suitable shape and the two phased array sensing units 108a, 108b have any suitable shape geometrically complimentary to the parts 304A, 304B.

Referring again to FIGS. 1, 3A-3B and 4A-4B, in one aspect, the two phased array sensing units 108a, 108b are mounted on (or to) the sensor support member 306 of the stationary sensor element 102. In one aspect, the sensor support member 306 provides movement of at least one of the phased array sensing units 108a, 108b relative to the another one of the phased array sensing units 108a, 108b between an open (e.g. loading) position and a closed (e.g. inspection) position. When in the open position, the part 304 can be loaded into, or positioned in the inspection apparatus 101 between the phased array sensing units 108a, 108b, and when in the closed position, the geometrically complimentary shape of the phased array sensing units 108a, 108b substantially surrounds at least a portion of the part 304 so as to prevent the part from exiting the stationary sensor element 102 in a direction Y that is parallel to (or substantially along the same plane as) a plane P of the part 304.

Figure 5A:
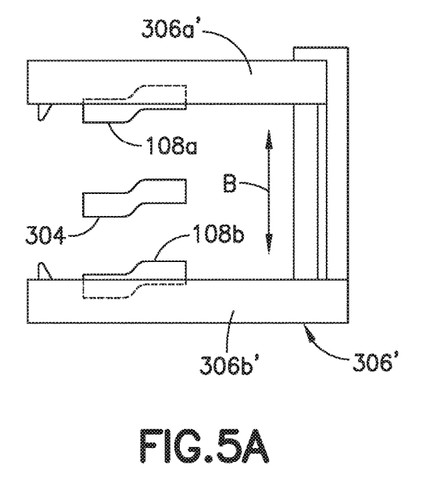
FIGS. 5A-5C are exemplary illustrations of the inspection system according to aspects of the present disclosure.
Figure 5B:
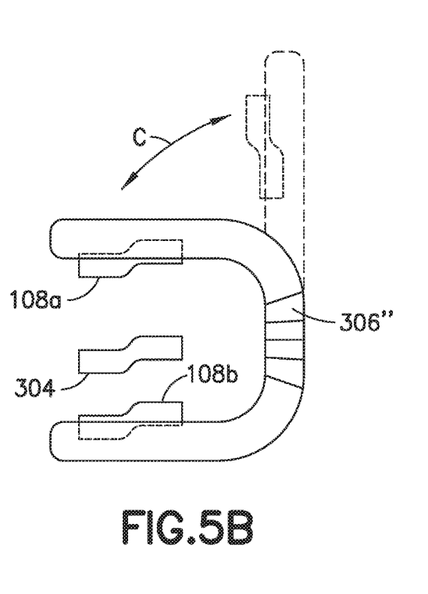
Figure 5C:
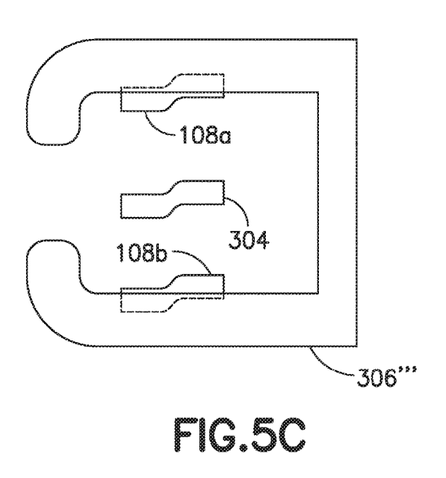
Figure 6:
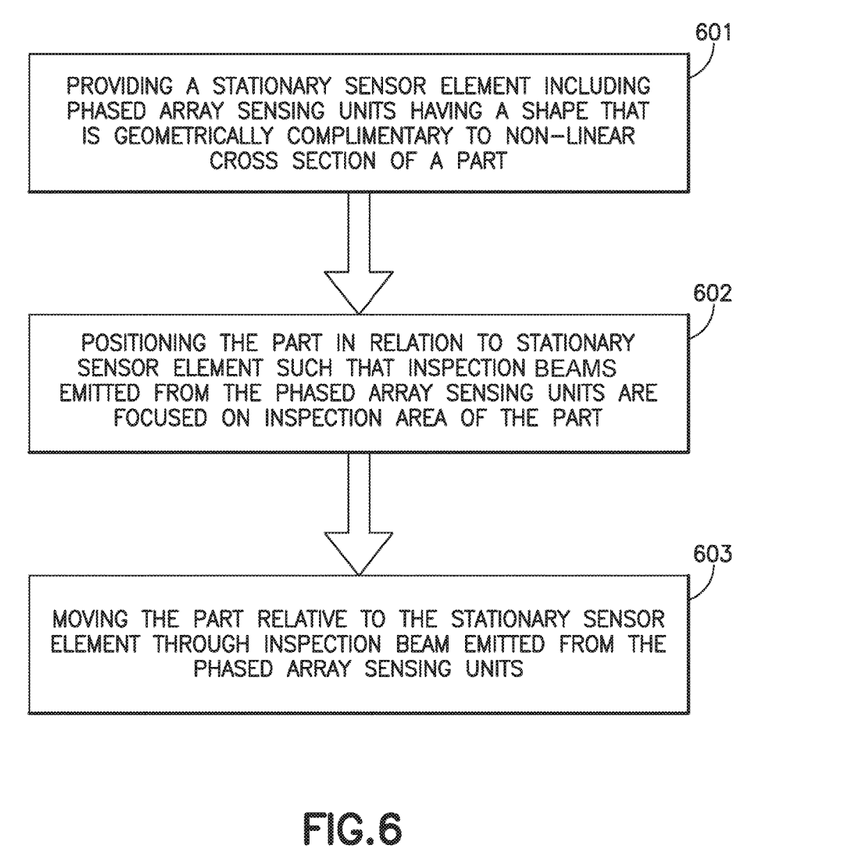
FIG. 6 is an exemplary method flow chart according to one or more aspects of the present disclosure.

In one aspect, the sensor support member 306 has a clamshell configuration with a top portion 306a and a bottom portion 306b (as shown in FIG. 3A and 3B for illustrative purposes only) joined together by a hinge 307. It is noted that the terms "top" and "bottom" are used herein for reference and that any other suitable spatial identifiers may be used. In one aspect, the phased array sensing unit 108a is mounted to the top portion 306a and the phased array sensing unit 108b is mounted to the bottom portion 306b. In other aspects, the sensor support member 306 has any suitable configuration which supports the part 304 so that the part 304 can be placed between the two phased array sensing units 108a, 108b. For example, in one aspect, the sensor support member 306 is a substantially single-piece sensor support member 306''' with no moving parts that accommodates the part 304 within itself (see FIG. 5C). In another aspect, as shown in FIG. 5A, the exemplary sensor support member 306' includes a linear slide so as to open in a linear fashion so that the part 304 is placed between the two phased array sensing units 108a, 108b. As illustrated in FIG. 5A, the top portion 306a' of the sensor support member 306' is able to lift or slide in the direction of arrow B relative to the bottom portion 306b'. In other aspects, one or more of the top portion 306a' and bottom portion 306b' are configured to slide relative to one another in any direction for loading the part 304 into the inspection apparatus 101. In yet other aspects, as shown in FIG. 5B, the sensor support member 306'' is flexible and flexes along a direction C. The flexible sensor support member 306'' is configured to be positioned around the part 304 so that the phased array sensing units 108a, 108b faces opposite sides of the part 304. In one aspect, the sensor support member 306'' includes stops (not shown) to repeatably position the two phased array sensing units 108a, 108b relative to the part 304 held in the stationary sensor 102. In yet other aspects, any suitable sensor support member supporting the two phased array sensing units 108a, 108b can be employed.

Referring still to FIGS. 1, 3A-3B and 4A-4B, the sensor support member 306 is mounted on, or supported on the frame 310 of the support 103. In other aspects, the sensor support member 306 is mounted separately from the frame 310 to a common base member (e.g. for example, the bottom of the catch tank 308, described in greater detail below). The frame 310 and support 103 forms the chassis of the inspection apparatus 101. In one aspect, the support 103 includes a drive assembly 104 configured to move the part 304 relative to the stationary sensor element 102, a frame 310 and one or more guide roller(s) 301. The drive assembly 104, in turn, includes the drive actuator 303 and one or more drive wheel(s) 302, which are connected to and driven by the drive actuator (or drive motor) 303. The drive wheel(s) 302 engages the part 304 to move the part 304 relative to the stationary sensor element 102 during an inspection process so that the part 304 moves through the ultrasonic inspection beam emitted from the two phased array sensing units 108a,

108b. In other aspects, the drive assembly 104 is located on (or mounted on) the common base member. In still other aspects, the drive assembly 104 is mounted to the sensor support member 306 so that the sensor support member 306 supports the part 304 during the inspection process. As described above, drive assembly 104 includes the drive actuator (or drive motor) 303, which is connected to one or more drive wheel(s) 302 that engage with and moves the part 304 along a direction A (see FIGS. 3A and 3B). In one aspect, the drive wheel(s) 302 engage the part 304 by friction in order to move the part 304 relative to the stationary sensor element 102. In other aspects, the drive assembly 104 includes any suitable drive assembly, including linear actuators, rotary drive systems connected to a drive wheel, drive casters, or other part engagement mechanism to move the part 304 relative to the stationary sensor 102. In other aspects, the part 304 is manually moved relative to the stationary sensor element 102.

In one aspect, the support 103 further includes one or more guide roller(s) 301, which guide the part 304 as the part 304 is moved through the stationary sensor element 102 by the drive wheel 302. In one aspect, one or more of the guide roller(s) 301 provide a biasing force against the part 304 to bias the part 304 in a predetermined direction, e.g. such as against the drive wheel(s) 302 to facilitate engagement between the drive wheel(s) 302 and the part 304. In one aspect, the one or more guide roller(s) 301 can include horizontal guide rollers 301a and 301b which prevent the part 304 from shifting or moving along a direction Y during the inspection process to maintain the concentricity of the radii of the curved portions 460, 480 of the phased array sensing units 108a, 108b with a respective radii of a respective curved portion of the part 304. The one or more guide roller(s) 301 can also include vertical guide rollers 301c which prevents the part 304 from shifting or moving along a direction Z during the inspection process. In one aspect, the guide roller(s) 301 can also be configured as casters, ball bearings or other components with low friction surfaces. In one aspect, the guide roller(s) 301 further accommodate the curvature of the part 304 as the part 304 is moved by the drive assembly 104 relative to the stationary sensor element 102. For example, the guide roller(s) 301 are mounted to the support 103 by pivoting member and/or axels 320-322 which can swivel or pivot the guide roller(s) 301 about an axis (see FIG. 3B), accommodating the curvature of the part 304. In other aspects, the drive wheel 302 are also mounted on a pivoting member 323 which also pivots or swivels the drive wheel 302 to accommodate the curvature of part 304 (functioning like, for example, a caster engaging the part 304 by friction).

In one aspect, the support 103 further includes, for example, a support roller 305, which supports a portion of the part 304 as the part 304 is moved or driven by the drive wheel(s) 302. In one aspect, the support roller 305 is positioned so that the drive wheel(s) 302 and support roller 305 form a platform to support the part 304 during the inspection process. In one aspect, the support roller 305 prevents the part 304 from shifting due to gravity during the inspection process and maintains, with the drive wheel(s) 302, the part 304 in a predetermined inspection orientation as the part 304 is being inspected. In one aspect, the support roller 305 is driven by the drive actuator 303, or other suitable drive, which drives the drive wheel 302 so that the support roller 305 rotates or drives the part 304 at substantially the same rate as the drive wheel(s) 302. In other aspects, the support roller 305 is passive and is not driven by any drive actuator or motor (e.g. the support roller 305 is an idler roller/wheel).

In one aspect of the present disclosure, the frame 310 of the inspection apparatus 101 is, in one aspect, disposed in the catch tank 308. In one aspect, the catch tank 308 is configured to contain a liquid ultrasonic medium such as, for example, water. In one aspect, the catch tank 308 includes a recirculating pump and filter 309 which recirculates the liquid ultrasonic medium and keeps the liquid ultrasonic medium clean. In one aspect, the recirculating pump and filter 309 further pumps liquid ultrasonic medium between (or otherwise causes a flow of the liquid ultrasonic medium between) the two phased array sensing units 108a, 108b and the part 304 to provide a transmission medium for the ultrasonic inspection beam.

In one aspect, the inspection apparatus 101 includes the controller 110. The controller 110 is connected to (and controls) one or more of the drive assembly 104 and the stationary sensor element 102 as described herein. In other aspects, the inspection apparatus 101 does not include the controller 110, and instead, one or more of the drive assembly 104 and the stationary sensor element 102 is controlled by an external controller such as, for example, the data acquisition and analysis computer 106 or data analysis computer 107. In one aspect, the controller 110, the data acquisition and data analysis computer 106 and/or the data analysis computer 107 controls the movement of the part 304 during the inspection process so as to prevent scanning the same portion of the part 304 more than once. In yet other aspects, the drive actuator 303 is controlled manually by switch and not by the controller 110.

Referring still to FIGS. 1, 3A-3B and 4A-4B, the inspection apparatus 101 is communicably connected to the interface 105. In one aspect, the interface 105 is an interface that receives data from the phased array sensing units 108 and/or the controller 110 and communicates the data to one or more of the data acquisition and data analysis computer 106 or the data analysis computer 107. In in one aspect, the interface 105 is, for example, the Focus PX™ interface for ultrasonic inspection systems. In other aspects, the interface 105 is any suitable interface between the inspection apparatus 101 and the data acquisition or data analysis computer 106 and/or data analysis computer 107.

The data acquisition and data analysis computer 106 provides for analysis of the data from the phased array sensing units 108a, 108b to detect or sense anomalies or defects within the part 304. In one aspect, the data acquisition and data analysis computer 106 controls some or all aspects of the operation of the inspection apparatus 101. In one aspect, the data acquisition and data analysis computer 106 controls some or all of the operation of the stationary sensor element 102 as previously described. In other aspects, the data acquisition and data analysis computer 106 controls the drive assembly 104 and the drive actuator 303 as previously described. In yet other aspects, the data acquisition and data analysis computer does not control any of the operations of the inspection apparatus 101 at all and instead acts as a data acquisition and analysis device.

In one aspect, the data acquisition and data analysis computer 106 is connected to another data analysis computer 107, which is substantially similar to the data acquisition and data analysis computer 106. In one aspect, this arrangement permits multiple users to analyze different sets of data within the inspection process. In other aspects, this arrangement permits multiple users to analyze the same set of data as part of the inspection process. In other aspects, the data analysis computer 107 is configured as a backup data analysis device with respect to the data acquisition and data analysis computer 106. In some aspects, the data analysis computer 107 and data acquisition and data analysis computer 106 are connected either serially or in parallel to the interface 105 (parallel connection shown in phantom) to effect connection of the data acquisition and data analysis computer 106 and data analysis computer 107 to the inspection apparatus 101. In yet other aspects, there is no data analysis computer 107.

Referring now to FIGS. 1, 3A-3B, 4A-4B and 6, an exemplary flow chart of the operations of the inspection system 100 is shown. At block 601, the stationary sensor element 102 is provided including phased array sensing units 108a, 108b each having a shape that is geometrically complementary to the non-linear cross section of the part 304 as described herein. At block 602, the part 304 is positioned in relation to the stationary sensor element 102 such that the inspection beam is emitted from the phased array sensing units 108a, 108b are focused on the inspection area of the part 304. In one aspect, the stationary sensor element 102 is opened (placed in the loading position) and the part 304 is positioned within the stationary sensor element 102 relative to the phased array sensing units 108a, 108b so that a curved section of the phased array sensing units 108a, 108b is substantially concentric with a radii of a curved portion of the part 304 as described above. In one aspect, as noted above, based on the geometry of the part 304 and the phased array sensing units 108a, 108b, the ultrasonic inspection beam is emitted from the phased array sensing units 108a, 108b at an angle that is substantially perpendicular to the surface of the inspection area of the part 304. At block 603, the part 304 is moved relative to the stationary sensor element 102 through the inspection beam emitted from the phased array sensing units 108a, 108b. In one aspect, the movement of the part 304 relative to the stationary sensor element 102 permits the part 304 to be scanned in substantially a single pass. For example, the controller 110, or in other aspects, the data acquisition and data analysis computer 106 and/or the data analysis computer 107, control the drive assembly 104 so that the drive wheel(s) 302 drive or move the part 304 through the stationary sensor element 102. As described above, in one aspect, the part 304 is a closed loop that includes curves or bends that lie in the plane P of the part 304, and the guide roller(s) 301 and the drive wheel(s) 302 provide for the rotation of the part 304 in the plane P along a direction A while maintaining the concentricity of the radii of the curved portions 460, 480 of the phased array sensing units 108a, 108b with a respective radii of a respective curved portion of the part 304. In one aspect, data obtained from scanning the part 304 is sent to the data acquisition and data analysis computer 106 and/or the data analysis computer 107 by the controller 110 (or in other aspects, from the phased array sensing units 108a, 108b) for the detection of and/or analysis of foreign materials, delaminations and porosity of the non-linear cross-section of the part 304 based on the scan data from the phased array sensing units 108a, 108b.

The disclosure and drawing figures describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, in some aspects of the disclosure, not all operations described herein need be performed.

Figure 7:
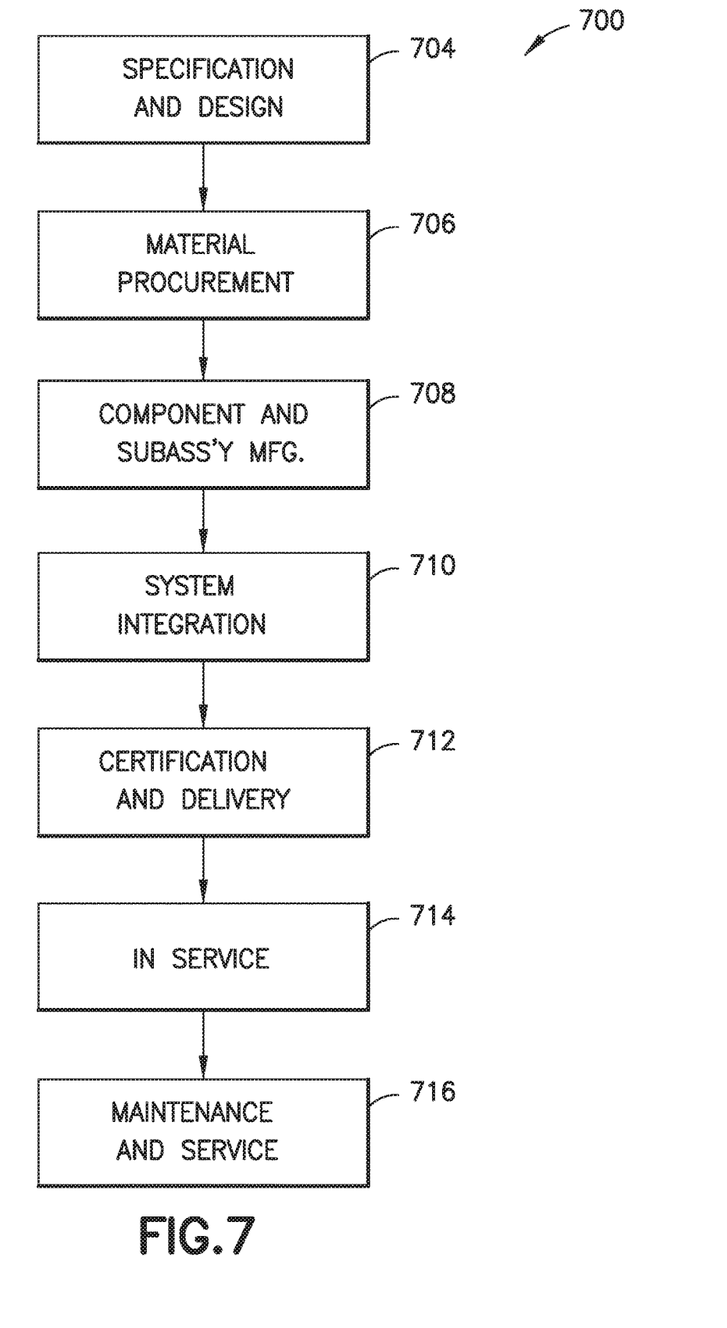
FIG. 7 is a flow diagram of aircraft production and service methodology in accordance with one or more aspects of the present disclosure.
Figure 8:
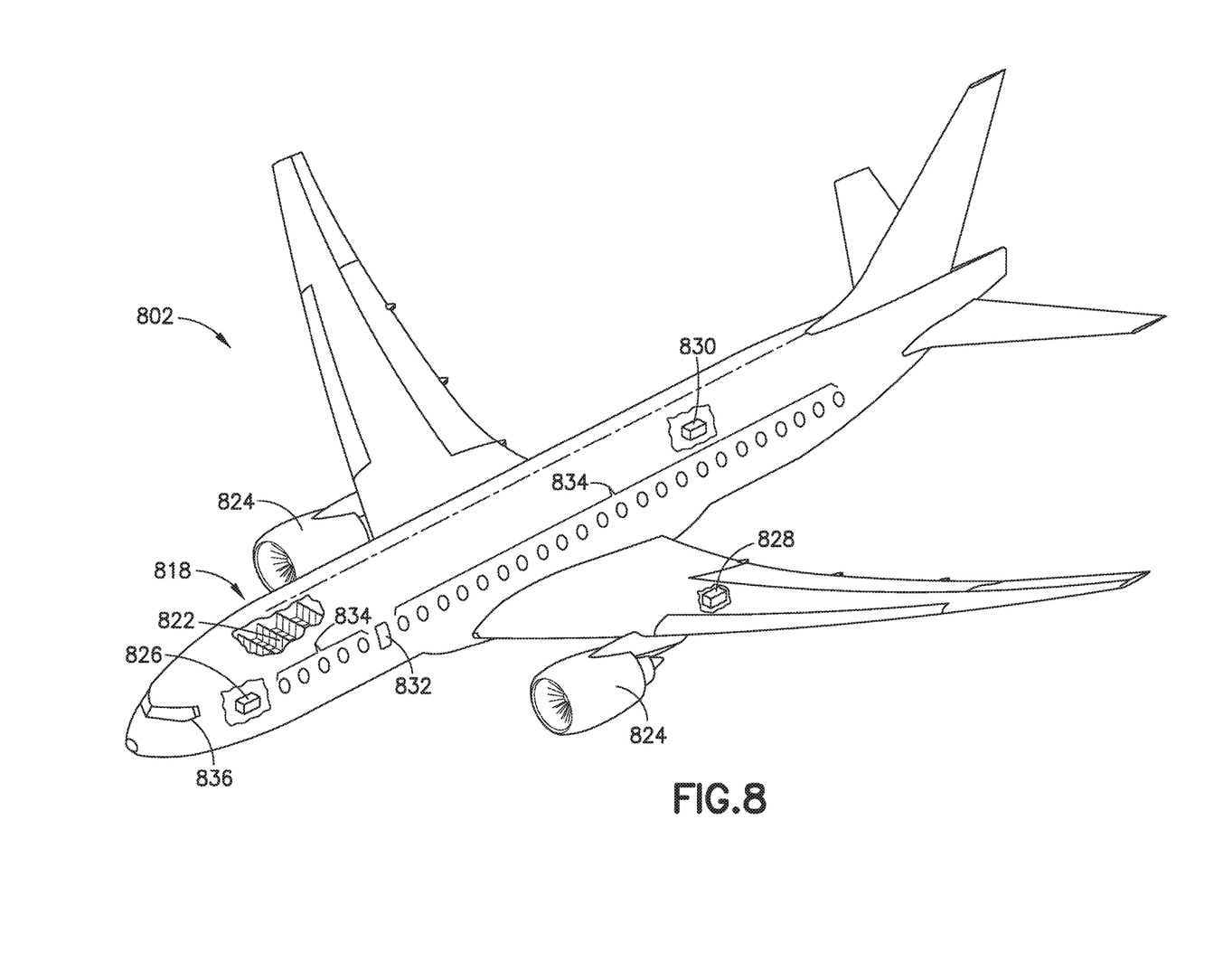
FIG. 8 is a schematic illustration of an aircraft in accordance with one or more aspects of the present disclosure.

Examples of the disclosure may be described in the context of an aircraft manufacturing and service method 700 as shown in FIG. 7, an aircraft 802 as shown in FIG. 8. In one aspect, the inspection system 100 described herein can be employed, for instance, in any stage of aircraft manufacturing and the components and structures inspected by the inspection system 100 may form any suitable part of an aircraft or component used in aircraft design and manufacture. During pre-production, the inspection system 100 may be employed during specification and design 704 and during material procurement 706, production, component and subassembly manufacturing 708 and system integration 710 stages. Thereafter, the aircraft 802 may go through certification and delivery 712 to be placed in service 714. While in service by a customer, the aircraft 802 is scheduled for routine maintenance and service 716 (which may also include modification, reconfiguration, refurbishment, and so on), which can result in further inspection of components and structures by the inspection system 100.

Each of the processes of the illustrative method 700 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 8, the aircraft 802 produced by the illustrative method 700 may include an airframe 818 with an interior 822. Examples of systems which may include components which can be inspected by inspection system 100 may include one or more of a propulsion system 824, an electrical system 826, a hydraulic system 828, and an environmental system 830. In other aspects, window frames 834, door frames 832 and cockpit windshield frames 836 can also be inspected with the inspection system 100. Any number of other systems may include components which are inspected by inspection system 100. Although an aerospace example is shown, the principles of the invention may be applied to other industries, such as the automotive and maritime industries.

Apparatus and methods shown or described herein may be employed during any one or more of the stages of the manufacturing and service method 700. For example, components or subassemblies corresponding to component and subassembly manufacturing 708 may be fabricated or manufactured in a manner similar to components or subassemblies produced while the aircraft 802 is in service. Also, one or more aspects of the apparatus, method, or combination thereof may be utilized during the production states 708 and 710, for example, by detecting and identifying defective parts 304 of an aircraft 802. Similarly, one or more aspects of the apparatus or method realizations, or a combination thereof, may be utilized, for example and without limitation, while the aircraft 802 is in service, e.g., maintenance and service 716 for inspection of parts 304 or replacement components In accordance with one or more aspects of the present disclosure, an apparatus for inspecting a part having a non-linear cross section includes a stationary sensor element including at least one phased array sensing unit, each of the at least one phased array sensing unit having a shape that is geometrically complimentary to the non-linear cross section of the part, and a support for the part having the non-linear cross section, the support comprising a drive assembly configured to move the part relative to the stationary sensor element, through an inspection beam emitted from the at least one phased array sensing unit.

In accordance with one or more aspects of the present disclosure, each of the at least one phased array sensing unit comprise at least one curved portion that is substantially concentric with a radii of at least one curved portion of the part held by the support.

In accordance with one or more aspects of the present disclosure, each of the at least one phased array sensing unit comprise at least one flat portion that is substantially parallel to at least one flat flange portion of the part held by the support.

In accordance with one or more aspects of the present disclosure, each of the at least one phased array sensing unit further comprises at least one ultrasonic pulse/echo transducer.

In accordance with one or more aspects of the present disclosure, the at least one phased array sensing unit is configured to emit the inspection beam substantially perpendicular to a surface of the non-linear cross section of the part In accordance with one or more aspects of the present disclosure, the drive assembly is configured to move the part through the inspection beam from the at least one phased array sensing unit, wherein the inspection beam from the at least one phased array sensing unit is focused on an inspection area of the part.

In accordance with one or more aspects of the present disclosure, the stationary sensor unit is configured to sense foreign material, delaminations and porosity of the non-linear cross section of the part.

In accordance with one or more aspects of the present disclosure, the non-linear cross section of the part is substantially a Z-beam cross-section.

In accordance with one or more aspects of the present disclosure, the part forms a closed loop shape.

In accordance with one or more aspects of the present disclosure, the part is a substantially open shape.

In accordance with one or more aspects of the present disclosure, the apparatus further includes a recirculating pump and a catch tank, wherein the catch tank is configured to contain a liquid ultrasonic signal medium and the recirculating pump is configured to pump the liquid ultrasonic signal medium through the stationary sensor element to enhance the inspection beam.

In accordance with one or more aspects of the present disclosure, the at least one phased array sensing unit includes at least one linear portion and at least one curved portion so as to form a substantially J-shaped array.

In accordance with one or more aspects of the present disclosure, the at least one phased array sensing unit includes two opposed phased array sensing units disposed on opposite sides of the part.

In accordance with one or more aspects of the present disclosure, each of the two opposed phased array sensing units is configured to scan a respective side of the part.

In accordance with one or more aspects of the present disclosure, the two opposed phased array sensing units are movable relative to each other.

In accordance with one or more aspects of the present disclosure, a system for inspecting a part having a non-linear cross section includes a stationary sensor element including at least one phased array sensing unit, each of the at least one phased array sensing unit having a shape that is geometrically complimentary to the non-linear cross section of the part, a support for the part having the non-linear cross section, the support comprising a drive assembly configured to move the part relative to the stationary sensor element, through an inspection beam emitted from the at least one phased array sensing unit, and a controller connected to the stationary sensor element and the drive assembly, the controller being configured to receive scan data from the stationary sensor element corresponding to the part.

In accordance with one or more aspects of the present disclosure, each of the at least one phased array comprise at least one curved portion that is substantially concentric with a radii of at least one curved portion of the part held by the support.

In accordance with one or more aspects of the present disclosure, each of the at least one phased array comprise at least one flat portion that is substantially parallel to at least one flat flange portion of the part held by the support.

In accordance with one or more aspects of the present disclosure, each of the at least one phased array further comprises an ultrasonic pulse/echo transducer.

In accordance with one or more aspects of the present disclosure, the at least one phased array sensing unit is configured to emit the inspection beam at a normal angle to a surface of the non-linear cross section of the part.

In accordance with one or more aspects of the present disclosure, the controller controls the drive assembly to move the part through the inspection beam from the at least one phased array sensing unit, wherein the inspection beam is focused on an inspection area of the part.

In accordance with one or more aspects of the present disclosure, the controller is configured to identify foreign material, delaminations and porosity of the non-linear cross section of the part based on the scan data from the stationary sensor element.

In accordance with one or more aspects of the present disclosure, the apparatus further includes a recirculating pump and a catch tank, wherein the catch tank is configured to contain a liquid ultrasonic signal medium and the recirculating pump is configured to pump the liquid ultrasonic signal medium through the stationary sensor element to enhance the inspection beam.

In accordance with one or more aspects of the present disclosure, the at least one phased array sensing unit includes at least one linear portion and at least one curved portion to form a substantially J-shaped array.

In accordance with one or more aspects of the present disclosure, the at least one phased array sensing unit includes two phased array sensing units disposed on opposite sides of the part.

In accordance with one or more aspects of the present disclosure, each of the two phased array sensing units is configured to scan one of the opposite sides of the part.

In accordance with one or more aspects of the present disclosure, the two phased array sensing units are movable relative to each other so that the part is placed between the two phased arrays.

In accordance with one or more aspects of the present disclosure, a method for inspecting a part having a non-linear cross section includes providing a stationary sensor element including at least one phased array sensing unit having a shape that is geometrically complimentary to the non-linear cross section of the part, positioning the part in relation to the stationary sensor element such that an inspection beam emitted from the at least one phased array sensing unit is focused on an inspection area of the part having the non-linear cross section, and moving the part relative to the stationary sensor element through the inspection beam emitted from the at least one phased array sensing unit.

In accordance with one or more aspects of the present disclosure, the inspection beam is an ultrasonic signal.

In accordance with one or more aspects of the present disclosure, the inspection beam is an ultrasonic pulse/echo signal.

In accordance with one or more aspects of the present disclosure, the method further includes detecting foreign material, delaminations and porosity of the non-linear cross section of the part based on a scan data from the at least one phased array sensing unit.

In accordance with one or more aspects of the present disclosure, the method further includes pumping a liquid ultrasonic signal medium through the at least one phased array sensing unit to enhance the inspection beam with a recirculating pump and a catch tank.

In accordance with one or more aspects of the present disclosure, the stationary sensor element scans the part in substantially a single pass.

In accordance with one or more aspects of the present disclosure, the part is positioned relative to the stationary sensor element so that a curved section of the stationary sensor element is substantially concentric with a radii of a curved portion of the part.

In accordance with one or more aspects of the present disclosure, the inspection beam emitted from the at least one phased array sensing unit is substantially perpendicular to the inspection area of the part having the non-linear cross-section.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings.

Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. An apparatus for inspecting a part having a non-linear cross section and a length including at least one curved portion, the apparatus comprising:
   a frame;
   a stationary sensor element that is fixed relative to the frame and includes at least one phased array sensing unit, each of the at least one phased array sensing unit having a shape that is geometrically complimentary to the non-linear cross section of the part;
   a support for the part, having the non-linear cross section and the length including the at least one curved portion, the support comprising a drive assembly configured to move the part, in a moving direction along the length of the part, relative to the stationary sensor element, through an inspection beam emitted from the at least one phased array sensing unit, where the drive assembly includes pivoting members that pivot relative to the stationary sensor element to conform to a changing curvature of the at least one curved portion, along the length of the part, as the part is moved relative to the stationary sensor element; and
   a sensor support member configured to support the stationary sensor element, the sensor support member having a first portion and a second portion, the second portion being separate and distinct from the first portion and positioned relative to the first portion so as to form a part receiving opening into which the part is placed.

2. The apparatus of claim 1, wherein each of the at least one phased array sensing unit comprise at least one curved portion that is substantially concentric with a radii of at least one curved portion of the part held by the support.

3. The apparatus of claim 1, wherein the at least one phased array sensing unit is configured to emit the inspection beam substantially perpendicular to a surface of the non-linear cross section of the part.

4. The apparatus of claim 1, wherein the non-linear cross section of the part is substantially a Z-beam cross-section.

5. The apparatus of claim 1, wherein the part forms a closed loop shape along a length of the part within a plane of the closed loop and the pivoting members pivot relative to the stationary sensor element to conform to a changing curvature of the closed loop shape, along the length of the part, as the part is moved relative to the stationary sensor element.

6. The apparatus of claim 1, wherein the at least one phased array sensing unit includes at least one linear portion and at least one curved portion so as to form a substantially J-shaped array.

7. The apparatus of claim 1, wherein the at least one phased array sensing unit includes two opposed phased array sensing units disposed on opposite sides of the part.

8. The apparatus of claim 7, wherein each of the two opposed phased array sensing units is configured to scan a respective side of the part.

9. The apparatus of claim 7, wherein the two opposed phased array sensing units are movable relative to each other.

10. A system for inspecting a part having a non-linear cross section and a length including at least one curved portion, the system comprising:
   a frame;
   a stationary sensor element that is fixed relative to the frame and includes at least one phased array sensing unit, each of the at least one phased array sensing unit having a shape that is geometrically complimentary to the non-linear cross section of the part;
   a support for the part having the non-linear cross section and the length including the at least one curved portion, the support comprising a drive assembly configured to move the part, in a moving direction along the length of the part, relative to the stationary sensor element, through an inspection beam emitted from the at least one phased array sensing unit, where the drive assembly includes pivoting members that pivot relative to the stationary sensor element to conform to a changing curvature of the at least one curved portion, along the length of the part, as the part is moved relative to the stationary sensor element;

a sensor support member configured to support the stationary sensor element, the sensor support member having a first portion and a second portion, the second portion being separate and distinct from the first portion and positioned relative to the first portion so as to form a part receiving opening into which the part is placed; and a controller connected to the stationary sensor element and the drive assembly, the controller being configured to receive scan data from the stationary sensor element corresponding to the part.

11. The system of claim 10, wherein each of the at least one phased array comprise at least one curved portion that is substantially concentric with a radii of at least one curved portion of the part held by the support.

12. The system of claim 10, wherein the at least one phased array sensing unit is configured to emit the inspection beam at a normal angle to a surface of the non-linear cross section of the part.

13. The system of claim 10, wherein the at least one phased array sensing unit includes at least one linear portion and at least one curved portion to form a substantially J-shaped array.

14. The system of claim 10, wherein the at least one phased array sensing unit includes two phased array sensing units disposed on opposite sides of the part.

15. The system of claim 14, wherein the two phased array sensing units are opposed phased array sensing units disposed on opposite sides of the part.

16. The system of claim 14, wherein the two phased array sensing units are movable relative to each other.

17. A method for inspecting a part having a non-linear cross section and a length including at least one curved portion, the method comprising:

providing a stationary sensor element that is fixed relative to an inspection apparatus frame and that includes at least one phased array sensing unit having a shape that is geometrically complimentary to the non-linear cross section of the part;

positioning the part in relation to the stationary sensor element such that an inspection beam emitted from the at least one phased array sensing unit is focused on an inspection area of the part having the non-linear cross section and the length including at least one curved portion; and moving the part, with a drive assembly in a moving direction along the length of the part, relative to the stationary sensor element through the inspection beam emitted from the at least one phased array sensing unit, where the drive assembly includes pivoting members that pivot relative to the stationary sensor element to conform to a changing curvature of the at least one curved portion, along the length of the part, as the part is moved relative to the stationary sensor element;

wherein the part is placed within the stationary sensor element through a part receiving opening of the stationary sensor element.

18. The method of claim 17, wherein the stationary sensor element scans the part in substantially a single pass.

19. The method of claim 17, wherein the part is positioned relative to the stationary sensor element so that a curved section of the stationary sensor element is substantially concentric with a radii of a curved portion of the part.

20. The method of claim 17, wherein the at least one phased array sensing unit is configured to emit the inspection beam substantially perpendicular to a surface of the non-linear cross section of the part.

* * * * *